(12) United States Patent
Hombo et al.

(10) Patent No.: US 10,018,545 B2
(45) Date of Patent: Jul. 10, 2018

(54) SUBSTRATE CLEANING APPARATUS AND METHOD EXECUTED IN THE SAME

(71) Applicant: EBARA CORPORATION, Tokyo (JP)

(72) Inventors: Teruaki Hombo, Tokyo (JP); Junji Kunisawa, Tokyo (JP)

(73) Assignee: EBARA CORPORATION, Tokyo (JP)

( * ) Notice: Subject to any disclaimer, the term of this patent is extended or adjusted under 35 U.S.C. 154(b) by 293 days.

(21) Appl. No.: 14/717,976

(22) Filed: May 20, 2015

(65) Prior Publication Data
US 2015/0338328 A1 Nov. 26, 2015

(51) Int. Cl.
B08B 1/00 (2006.01)
G01N 3/56 (2006.01)
H01L 21/67 (2006.01)

(52) U.S. Cl.
CPC .............. *G01N 3/56* (2013.01); *B08B 1/006* (2013.01); *H01L 21/67046* (2013.01); *H01L 21/67051* (2013.01); *H01L 21/67253* (2013.01)

(58) Field of Classification Search
CPC .................................... G01N 3/56; B08B 1/04
See application file for complete search history.

(56) References Cited

U.S. PATENT DOCUMENTS 5,475,889 A * 12/1995 Thrasher ................... B08B 1/04
15/77
5,636,401 A 6/1997 Yonemizu et al.
8,083,571 B2 * 12/2011 Nabeya ................... B24B 37/30
451/10
2005/0067104 A1 3/2005 Takahara et al.
2008/0289652 A1 * 11/2008 Hamada ............ H01L 21/67057
134/6
2013/0199580 A1 8/2013 Zhang
2015/0221531 A1 8/2015 Tanaka

FOREIGN PATENT DOCUMENTS

| JP | H07-307321 A | 11/1995 |
|----|--------------|---------|
| JP | H10-223596 A | 8/1998 |
| JP | 10307504 A * | 11/1998 |
| JP | 2005-103450 A | 4/2005 |
| JP | 2006-007054 A | 1/2006 |
| JP | 2006-255851 A | 9/2006 |

(Continued)

OTHER PUBLICATIONS

Japan Patent Application No. 2014-104471; Reasons for Refusal; dated Apr. 16, 2018; 6 pages.

*Primary Examiner* — Erika J Villaluna
(74) *Attorney, Agent, or Firm* — Baker & Hostetler LLP

(57) ABSTRACT

A substrate cleaning apparatus 1 includes a cleaning member 2 that abuts on a substrate W to scrub and clean the substrate W, a holding member 6 that holds the cleaning member 2, an air cylinder 8 that generates force to press the cleaning member 2 against the substrate W, a displacement sensor 9 that measures a position of the holding member 6, and a control device 11 that determines the replacement time of the cleaning member 2 based on the position of the holding member 6. The position of the holding member 6 includes a cleaning position and a non-cleaning position. The control device 11 determines the replacement time of the cleaning member 2 from change in the cleaning position while a plurality of substrates W are continuously scrubbed and cleaned.

13 Claims, 12 Drawing Sheets

(56) References Cited

FOREIGN PATENT DOCUMENTS

| JP | 2008-515171 A | 5/2008 |
|----|---------------|--------|
| JP | 2009-099906 A | 5/2009 |
| JP | 2010-074191 A | 4/2010 |
| JP | 2014-038983 A | 2/2014 |
| WO | WO 2006/035624 A1 | 4/2006 |

\* cited by examiner (a)

(b)

(c)

(a)

(b)

PROJECTION LOSS

SUBSTRATE CLEANING APPARATUS AND METHOD EXECUTED IN THE SAME

CROSS-REFERENCE TO RELATED APPLICATIONS

This application claims the benefit of Japanese Priority Patent Application JP 2014-104471 filed on May 20, 2014, the entire contents of which are incorporated herein by reference.

FIELD

This technology relates to a substrate cleaning apparatus that brings a cleaning member into contact with a substrate to scrub and clean the substrate and a method executed in the substrate cleaning apparatus, and particularly relates to a technology for determining a replacement time of the cleaning member.

BACKGROUND AND SUMMARY

Conventionally, as a method that cleans the surface of a substrate such as a semiconductor substrate, a scrubbing cleaning method is used that rubs a substrate surface with a cleaning member having a brush, a sponge or the like while supplying deionized water to the substrate surface in order to clean the substrate surface. However, in this kind of scrubbing and cleaning, because the cleaning member is directly brought into contact with a substrate to clean the substrate, deformation and wear occurs in the cleaning member due to long time use, and as a result, the contact state of the cleaning member with the substrate changes and cleaning effectiveness is decreased.

Therefore, conventionally, a method of checking the contact state of a cleaning member has been proposed that uses a workpiece for checking to determine the contact state of the cleaning member from a contact trace of the cleaning member transferred to the workpiece for checking. For example, Japanese Patent Laid Open No. 2006-7054, Japanese Patent Laid Open No. 2010-74191 and Japanese Patent No. 4511591 describe such a technology. In such a manner, the contact state of the cleaning member is grasped and maintenance (for example, replacement of the cleaning member) is performed only when necessary.

However, in the conventional method, it is necessary to use a workpiece for checking to determine a replacement time of a cleaning member, which accordingly costs time and money by that amount, resulting in problems such as reduction of throughput and a cost increase.

It is desired to provide a substrate cleaning apparatus capable of appropriately determining a replacement time of a cleaning member with a high throughput and a decreased cost compared to the conventional substrate cleaning apparatus.

A substrate cleaning apparatus of one aspect includes a cleaning member that abuts on a substrate to scrub and clean the substrate, a holding means that holds the cleaning member, a pressing means that is provided in the holding means and generates force to press the cleaning member against the substrate, a position measuring means that is provided in the holding means and measures a position of the holding means and a replacement time determining means that determines a replacement time of the cleaning member based on the position of the holding means, in which the position of the holding means includes a cleaning position at which the cleaning member abuts on the substrate and a non-cleaning position where the cleaning member stays away from the substrate, and the replacement time determining means determines the replacement time of the cleaning member from change in the cleaning position while a plurality of substrates are continuously scrubbed and cleaned.

A substrate cleaning apparatus of another aspect includes a cleaning member that abuts on a substrate to scrub and clean the substrate, a holding means that holds the cleaning member, a pressing means that is provided in the holding means and generates force to press the cleaning member against the substrate, a position measuring means that is provided in the holding means and measures a position of the holding means and an abnormality detecting means that detects presence/absence of abnormality in the cleaning member based on the position of the holding means, in which the position of the holding means includes a cleaning position at which the cleaning member abuts on the substrate and a non-cleaning position where the cleaning member stays away from the substrate, and the abnormality detecting means detects presence/absence of abnormality in the cleaning member from change in the cleaning position while a single substrate is scrubbed and cleaned.

A replacement time determining method of another aspect is a replacement time determining method of a cleaning member in a substrate cleaning apparatus that scrubs and cleans a substrate, the replacement time determining method including a measuring step that measures a position of a holding means that holds the cleaning member and a determining step that determines a replacement time of the cleaning member based on the position of the holding means, in which the position of the holding means that holds the cleaning member includes a cleaning position at which the cleaning member abuts on the substrate and a non-cleaning position where the cleaning member stays away from the substrate, and the determining step determines the replacement time of the cleaning member from change in the cleaning position while a plurality of substrates are continuously scrubbed and cleaned.

An abnormality detecting method of yet another aspect is an abnormality detecting method in a cleaning member of a substrate cleaning apparatus that scrubs and cleans a substrate, the abnormality detecting method including a measuring step that measures a position of a holding means that holds the cleaning member and a detecting step that detects presence/absence of abnormality in the cleaning member based on the position of the holding means, in which the position of the holding means that holds the cleaning member includes a cleaning position at which the cleaning member abuts on the substrate and a non-cleaning position where the cleaning member stays away from the substrate, and the detecting step detects presence/absence of abnormality in the cleaning member from change in the cleaning position while a single substrate is scrubbed and cleaned.

DETAILED DESCRIPTION OF NON-LIMITING EXAMPLE EMBODIMENTS

Figure 1:
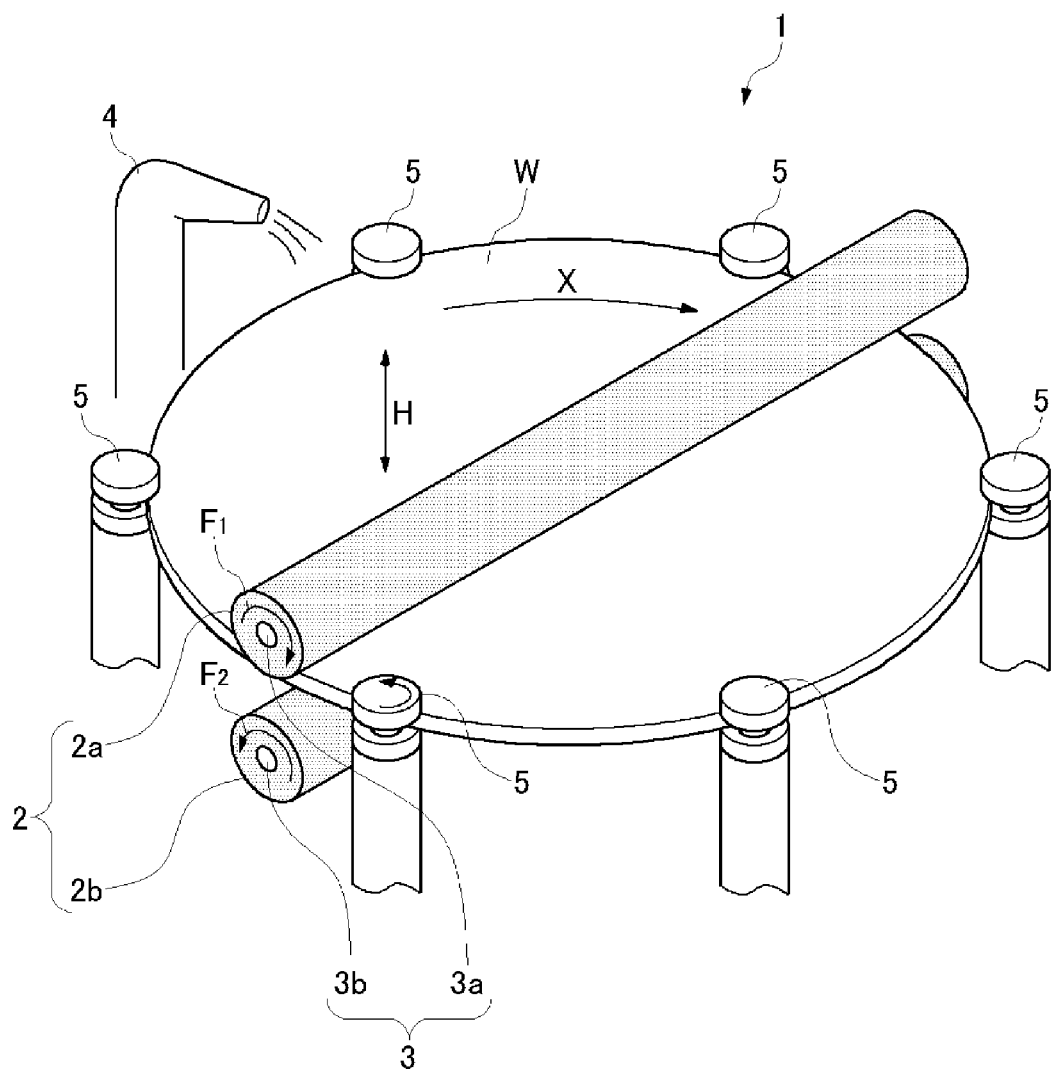
FIG. 1 is a perspective view illustrating a configuration of a substrate cleaning apparatus in this embodiment.

Now, a substrate cleaning apparatus of an embodiment will be described below. Note that the embodiment to be described below shows one example where this technology is implemented, and this technology should not be limited to a specific configuration to be described below. When this technology is implemented, a specific configuration may be appropriately adopted depending on embodiments.

A substrate cleaning apparatus of one embodiment includes a cleaning member that abuts on a substrate to scrub and clean the substrate, a holding means that holds the cleaning member, a pressing means that is provided in the holding means and generates force to press the cleaning member against the substrate, a position measuring means that is provided in the holding means and measures a position of the holding means and a replacement time determining means that determines a replacement time of the cleaning member based on the position of the holding means, in which the position of the holding means includes a cleaning position at which the cleaning member abuts on the substrate and a non-cleaning position where the cleaning member stays away from the substrate, and the replacement time determining means determines the replacement time of the cleaning member from change in the cleaning position while a plurality of substrates are continuously scrubbed and cleaned.

According to this configuration, when a substrate is scrubbed and cleaned, as a pressing amount of the cleaning member against the substrate (a crushed amount of the cleaning member), the cleaning position of the holding means is measured (the position of the holding means when the cleaning member abuts on the substrate). The cleaning member deforms and wears while continuously used and the pressing amount (the crushed amount) becomes large. Accordingly, while a plurality of substrates are continuously cleaned, the cleaning position of the holding means (the pressing amount of the cleaning member) changes. Therefore, the replacement time of the cleaning member can be appropriately determined from change in the cleaning position while the plurality of substrates are continuously scrubbed and cleaned.

Also, in the above substrate cleaning apparatus, the replacement time determining means may determine that the replacement time of the cleaning member is reached when an amount of change in the cleaning position becomes greater than a predetermined reference value.

In such a situation, while a plurality of substrates are continuously scrubbed and cleaned, when the amount of change in the cleaning position becomes greater than the predetermined reference value, it is determined that the replacement time of the cleaning member is reached. As described above, the amount of change in the cleaning position is compared with the predetermined reference value and the replacement time of the cleaning member can be appropriately determined.

The above substrate cleaning apparatus includes a cleaning member that abuts on a substrate to scrub and clean the substrate, a holding means that holds the cleaning member, a pressing means that is provided in the holding means and generates force to press the cleaning member against the substrate, a position measuring means that is provided in the holding means and measures a position of the holding means and an abnormality detecting means that detects presence/absence of abnormality in the cleaning member based on the position of the holding means, in which the position of the holding means includes a cleaning position at which the cleaning member abuts on the substrate and a non-cleaning position where the cleaning member stays away from the substrate, and the abnormality detecting means detects presence/absence of abnormality in the cleaning member from change in the cleaning position while a single substrate is scrubbed and cleaned.

According to this configuration, when a substrate is scrubbed and cleaned, as the pressing amount of the cleaning member against the substrate (a crushed amount of the cleaning member), the position of the holding means of the cleaning member is measured. For example, while the cleaning member is continuously used, a partial loss may occur in the surface of the cleaning member, and in such a situation, oscillation occurs due to the loss while the substrate is cleaned, and the loss occurrence is detected as change in the cleaning position of the holding means (the position of the holding means when the cleaning member abuts on the substrate). Thus, presence/absence of abnormality (occurrence of a partial loss and the like) in the cleaning member can be appropriately detected from the change in the cleaning position while a single substrate is cleaned.

Also, in the above substrate cleaning apparatus, the abnormality detecting means may detect that there is abnormality in the cleaning member when the amount of change in the cleaning position becomes greater than a predetermined reference amplitude.

In such a situation, while a single substrate is scrubbed and cleaned, when the amount of change in the cleaning position becomes greater than the predetermined reference amplitude, it is determined that there is abnormality in the cleaning member. As described above, the amount of change in the cleaning position is compared with the predetermined reference amplitude and presence/absence of abnormality in the cleaning member can be appropriately determined.

Furthermore, in the above substrate cleaning apparatus, the position measuring means is a displacement sensor that utilizes a position measurement laser beam, in which the holding means may be provided with a position measuring bracket that is irradiated with the position measurement laser beam.

In such a situation, when the position measuring bracket provided in the holding means is irradiated with the position measurement laser beam, reflected light (position measurement laser beam) from the position measuring bracket is detected by the displacement sensor, and from the detection result, the position of the holding means is measured. Thus, the position of the holding means (cleaning position) can be contactlessly measured.

Additionally, in the above substrate cleaning apparatus, two cleaning members are placed above and below a substrate so that the substrate is put between them, and a noise removing means may be provided that removes a noise on measuring the cleaning position by a difference processing of change in the cleaning position of the two cleaning members when the substrate is put between the two cleaning members, scrubbed and cleaned.

According to this configuration, when a substrate is put between two cleaning members placed above and below the substrate and cleaned, the position of the holding means (cleaning position) of respective cleaning members is measured. When the substrate is cleaned by using the cleaning member, a vibration noise may occur. This vibration noise is a very small oscillation compared with the oscillation occurring when there is a partial loss in the cleaning member. Because the vibration noise is thought to occur to a similar degree in the two cleaning members placed above and below the substrate, the vibration noise can be removed (canceled) by the difference processing of change in the cleaning position of the holding means of the two cleaning members. This can allow the change in the position of the holding means (cleaning position) to be measured with a high accuracy.

Also, the above substrate cleaning apparatus may include a load measuring means that measures force to press the cleaning member against a substrate and a load control means that controls the force to press the cleaning member against the substrate by feeding back the measured result of the load measuring means.

In such a situation, the force to press the cleaning member against the substrate is measured by the load measuring means and the force to press the cleaning member against the substrate can be controlled by feeding back the measured result (actually pressing force). Accordingly, the actually pressing force can be compared with a deformation amount of the cleaning member, allowing management to be performed with a higher accuracy.

A method of one embodiment is a replacement time determining method of a cleaning member in a substrate cleaning apparatus that scrubs and cleans a substrate, the replacement time determining method including a measuring step that measures a position of a holding means that holds the cleaning member and a determining step that determines a replacement time of the cleaning member based on the position of the holding means, in which the position of the holding means that holds the cleaning member includes a cleaning position at which the cleaning member abuts on the substrate and a non-cleaning position where the cleaning member stays away from the substrate, and the determining step determines the replacement time of the cleaning member from change in the cleaning position while a plurality of substrates are continuously scrubbed and cleaned.

Also according to this method, the replacement time of the cleaning member can be appropriately determined from the change in the cleaning position of the holding means while a plurality of substrates are continuously scrubbed and cleaned.

Furthermore, the above replacement time determining method may include a load measuring step that measures force to press the cleaning member against a substrate and a load control step that controls the force to press the cleaning member against the substrate by feeding back the measured result of the load measuring step.

In such a situation, the force to press the cleaning member against the substrate is measured and the force to press the cleaning member against the substrate can be controlled by feeding back the measured result (actually pressing force). Accordingly, the actually pressing force can be compared with the deformation amount of the cleaning member, allowing the replacement time to be determined with a higher accuracy.

Also, a method of one embodiment is an abnormality detecting method in a cleaning member of a substrate cleaning apparatus that scrubs and cleans a substrate, the abnormality detecting method including a measuring step that measures a position of a holding means that holds the cleaning member and a detecting step that detects presence/absence of abnormality in the cleaning member based on the position of the holding means, in which the position of the holding means that holds the cleaning member includes a cleaning position at which the cleaning member abuts on the substrate and a non-cleaning position where the cleaning member stays away from the substrate, and the detecting step detects presence/absence of abnormality in the cleaning member from change in the cleaning position while a single substrate is scrubbed and cleaned.

Also according to this method, presence/absence of abnormality (for example, occurrence of a partial loss) in the cleaning member can be appropriately detected from the change in the cleaning position of the holding means while a single substrate is cleaned.

According to the above embodiments, while a plurality of substrates are continuously scrubbed and cleaned, the replacement time of the cleaning member can be appropriately determined from the change in the position of the holding means (cleaning position). In such a situation, it is not necessary to use a workpiece for checking as in the conventional, allowing an enhanced throughput and a decreased cost by that amount to be achieved.

Embodiments

Now, a substrate cleaning apparatus of this embodiment will be described below with reference to the drawings. This embodiment will illustrate a substrate cleaning apparatus that is used, for example, to scrub and clean a substrate required to have a high cleaning level, such as a semiconductor substrate, a glass substrate and a liquid crystal panel.

A configuration of the substrate cleaning apparatus of this embodiment will be described with reference to the drawings. FIG. 1 is a view illustrating the configuration of the substrate cleaning apparatus of this embodiment. As shown in FIG. 1, a substrate cleaning apparatus 1 grasps and rotates a substrate W such as a semiconductor substrate to clean both surfaces of the substrate W by using a cleaning member 2. The substrate cleaning apparatus 1 includes a plurality of spindles 5 that support and rotate the circumferential edge portion of the substrate W, foamed polyurethane attached to cover the entire circumference of a shaft 3 (3a, 3b) and formed in an about columnar form, a cleaning member 2 (2a, 2b) formed from a roll sponge made of PVA or the like, and a cleaning liquid supply nozzle 4 that supplies a cleaning liquid such as ultra-pure water to the upper surface of the substrate W. The cleaning member 2 is configured to move up and down as shown by the arrow H and rotate about the shaft 3 around the shaft center of the shaft 3 as shown by the arrows F1, F2.

Also, to the spindle 5, a drive unit such as a motor is connected, and all of the spindles 5 rotate at an equal number of revolutions to rotate the substrate W at a predetermined number of revolutions. Note that at least one of the spindles 5 may be configured to self-rotate and the others to rotate in a driven manner.

A material of the cleaning member 2 is not limited to a sponge-like material, and the cleaning member 2 may be, for example, a member to which surface abrasive-coated textile is attached. As the cleaning member 2, a roll sponge having a cylindrically-shaped cleaning surface is used. The surface of the cylindrical portion of the cleaning member 2 is provided with a plurality of projection portions extending in the same direction as the cylindrical portion, made from the same material and shaped in a columnar form having a small diameter. On cleaning, these projection portions are pressed against the substrate W, allowing a cleaning effect on the substrate W to be enhanced.

In this substrate cleaning apparatus 1, in the state where the cleaning members 2 is moved by the drive unit in the direction perpendicular to the substrate W and shelters, the substrate W is chucked, held and rotated by the spindles 5 in the direction shown by the arrow X in FIG. 1. Then, while the cleaning members 2 are rotated at a predetermined number of revolutions, the cleaning members 2 are moved up or down to abut on the upper and lower surfaces of the substrate W by a predetermined press force or pressing amount, thereby rubbing both surfaces of the substrate W with these cleaning members to clean the both surfaces.

Also, on cleaning, a cleaning liquid (ultra-pure water and a medical solution such as ionized water, dilute hydrofluoric acid or hydrogen peroxide water) is sprayed from the cleaning liquid supply nozzle 4 to the upper surface of the substrate W, and simultaneously the cleaning liquid is also sprayed from a cleaning liquid supply nozzle provided below the substrate W and not shown to the lower surface of the substrate W.

Figure 2:
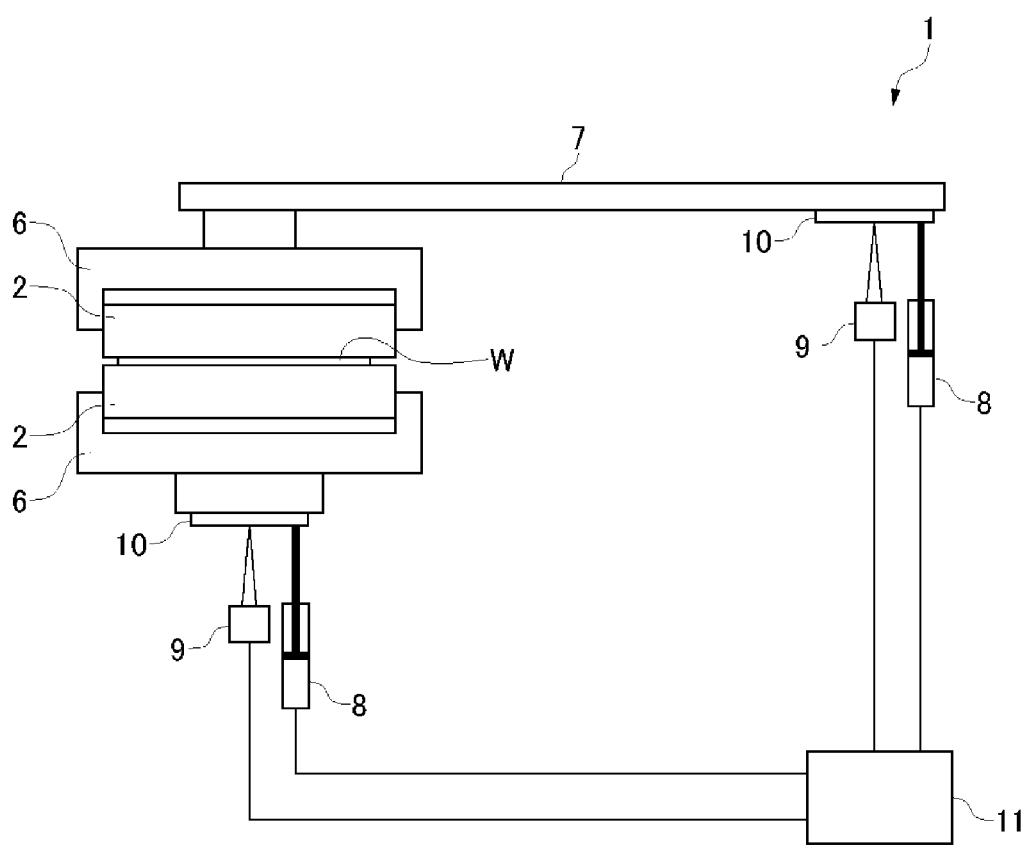
FIG. 2 is an illustration showing the configuration of the substrate cleaning apparatus in this embodiment.

FIG. 2 is an illustration of the substrate cleaning apparatus of this embodiment. As shown in FIG. 2, the cleaning member 2 is held by a holding member 6. In the example in FIG. 2, from an upper holding member 6, an arm 7 extends. And, the arm 7 is provided with an air cylinder 8 that generates force to press the cleaning member 2 against a substrate W. Furthermore, the arm 7 is provided with a position measuring bracket 10 which is irradiated with a position measurement laser beam from a displacement sensor 9. The displacement sensor 9 has a function that detects reflected light (position measurement laser beam) from the position measuring bracket 10 and measures a position of the arm 7 (and the upper holding member 6). Operation of the air cylinder 8 and the displacement sensor 9 is controlled by a control device 11.

On the one hand, a lower holding member 6 is not provided with an arm. In such a situation, the holding member 6 is provided with the air cylinder 8 that generates force to press the cleaning member 2 against a substrate W. Also, the holding member 6 is provided with the position measuring bracket 10 which is irradiated with the position measurement laser beam from the displacement sensor 9. The displacement sensor 9 has a function that detects reflected light (position measurement laser beam) from the position measuring bracket 10 and measures a position of the lower holding member 6. This operation of the air cylinder 8 and the displacement sensor 9 is also controlled by the control device 11.

The control device 11 has a function that determines a replacement time of the upper cleaning member 2 based on the position of the arm 7 (and the upper holding member 6) and a function that determines a replacement time of the lower cleaning member 2 based on the position of the lower holding member 6. Furthermore, the control device 11 has a function that detects presence/absence of abnormality in the upper cleaning member 2 based on the position of the arm 7 (and the upper holding member 6) and a function that detects presence/absence of abnormality in the lower cleaning member 2 based on the position of the lower holding member 6. A replacement time determining method and an abnormality detecting method will be described below in detail with reference to the drawings.

Here, the upper holding member 6 and the arm 7, and the lower holding member 6 correspond to the holding means, respectively. Additionally, the air cylinder 8 corresponds to the pressing means, and the displacement sensor 9 corresponds to the position measuring means. Furthermore, the control device 11 corresponds to the replacement time determining means and the abnormality detecting means.

Figure 3:
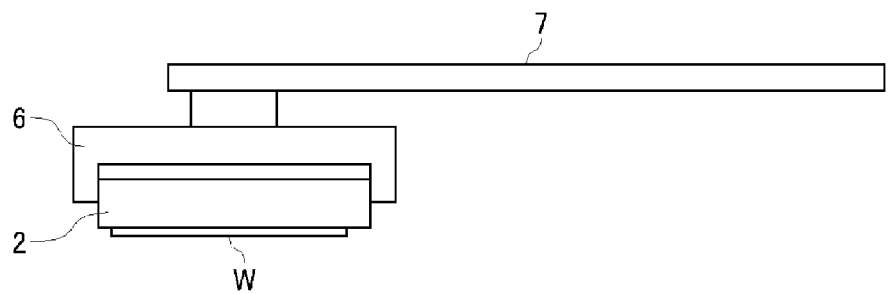
FIG. 3 is an illustration of a cleaning member and a position of a holding means in this embodiment.
Figure 3:
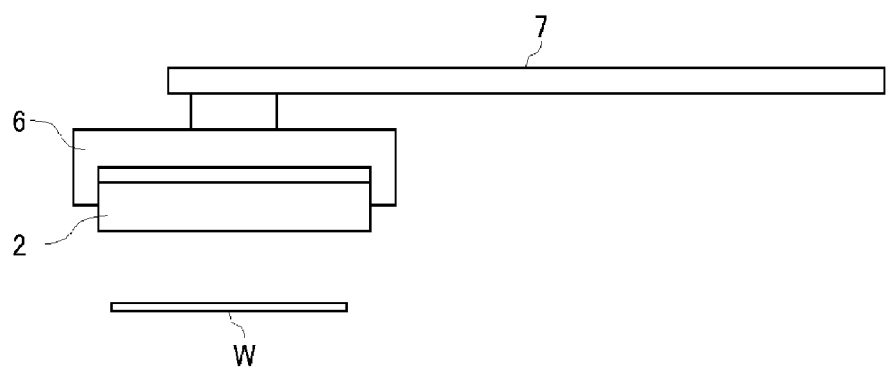
Figure 3:
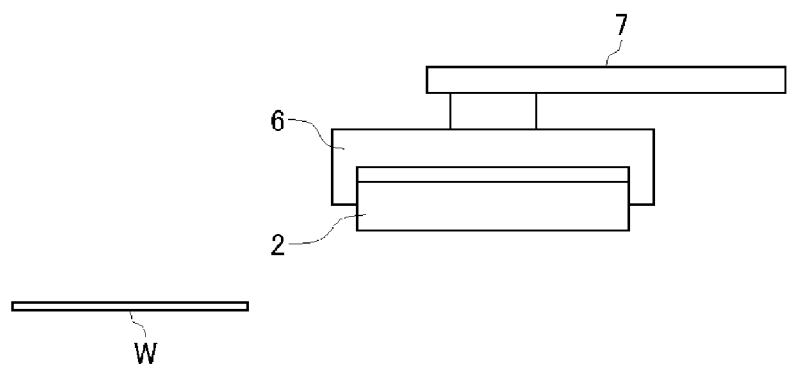

FIG. 3 is an illustration of the position of the cleaning member 2 and the holding member 6. In FIG. 3(A), the cleaning member 2 abuts on a substrate W. This position is a position at which the cleaning member 2 is pressed against the substrate W by a constant pressure and the substrate W is cleaned. This position of the cleaning member 2 is called a cleaning position. A position of the holding member 6 when the cleaning member 2 abuts on the substrate (when the cleaning member 2 is at the cleaning position) is called a "cleaning position".

In FIG. 3(B), the cleaning member 2 is placed above and away from the substrate W. This position is a position at which the cleaning member 2 begins to rotate. This position of the cleaning member 2 is called an upper position. Also, in FIG. 3(C), the cleaning member 2 is placed further away to the right side. This position is a position at which the cleaning member 2 stands by. This position of the cleaning member 2 is called a standby position. A position of the holding member 6 when the cleaning member 2 stays away from the substrate (when the cleaning member 2 is at the upper position or the standby position) is called a "non-cleaning position".

Figure 4:
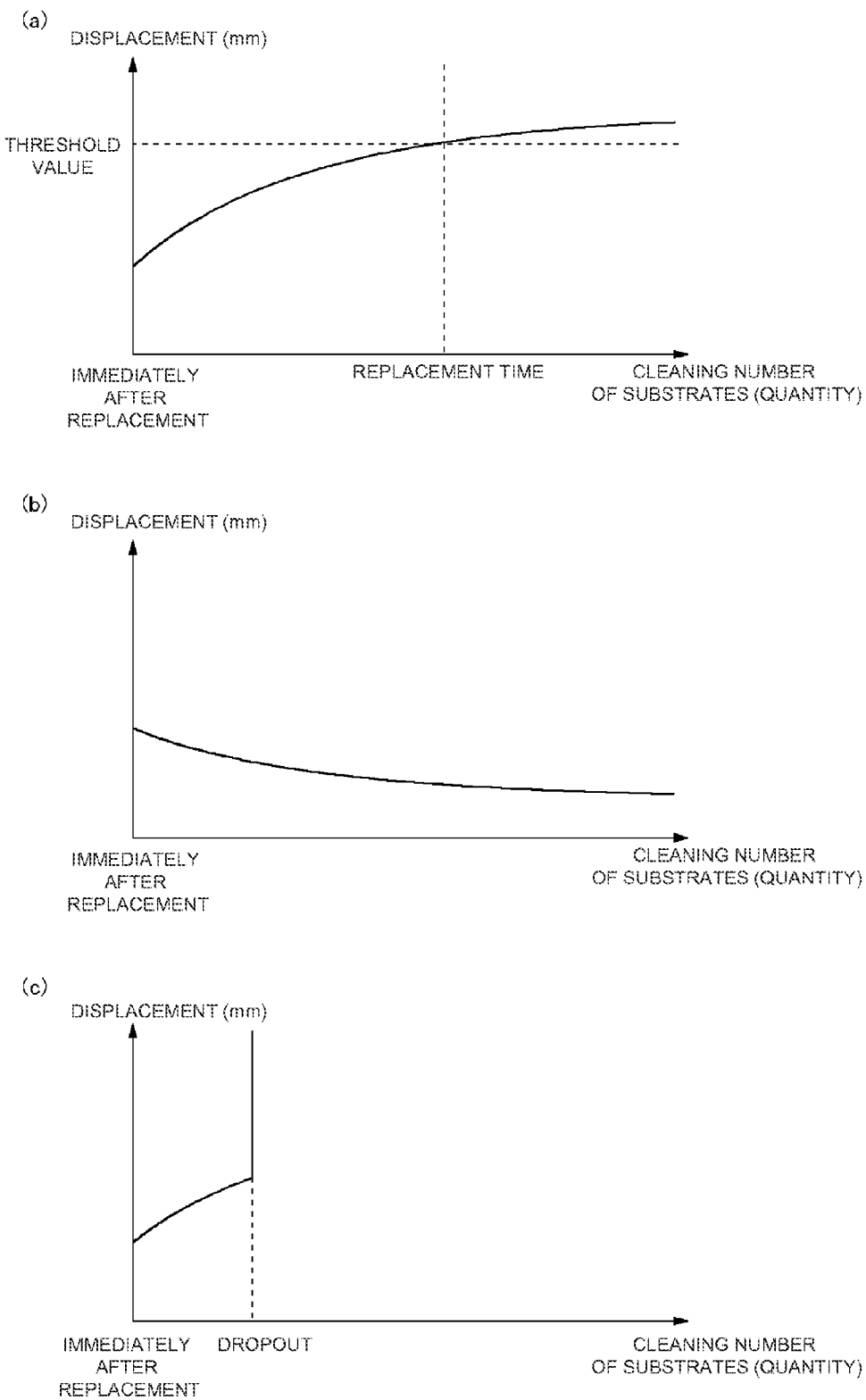
FIG. 4 is a view illustrating change in a cleaning position of the holding means (displacement) while a plurality of substrates are continuously cleaned in this embodiment.

The control device 11 determines the replacement time of the cleaning member 2 from change in the cleaning position while a plurality of substrates W are continuously scrubbed and cleaned. In particular, when an amount of change in the cleaning position becomes greater than a predetermined reference value, the control device 11 determines that the replacement time of the cleaning member 2 is reached. FIG. 4 is a view illustrating the change in the cleaning position (displacement) while a plurality of substrates are continuously cleaned. As shown in FIG. 4(A), every time a plurality of substrates W are cleaned, the change in the cleaning position (displacement) is measured by the displacement sensor 9. That is, a difference (displacement) from an initial value of the cleaning position (a position immediately after the cleaning member 2 is replaced) is measured, and when the difference (displacement) becomes greater than the predetermined reference value (threshold value), the control device 11 determines that the replacement time of the cleaning member 2 is reached. It is thought that after the cleaning member 2 is used for a long period, the sponge gradually softens and the cleaning position lowers.

Note that, from the change in the cleaning position while a plurality of substrates W are continuously scrubbed and cleaned, as shown in FIG. 4(B), abnormality that the sponge of the cleaning member 2 hardens due to an effect of a medical agent or the like can be also detected. Furthermore, as shown in FIG. 4(c), abnormality that the cleaning member 2 drops off can be also detected.

Figure 5:
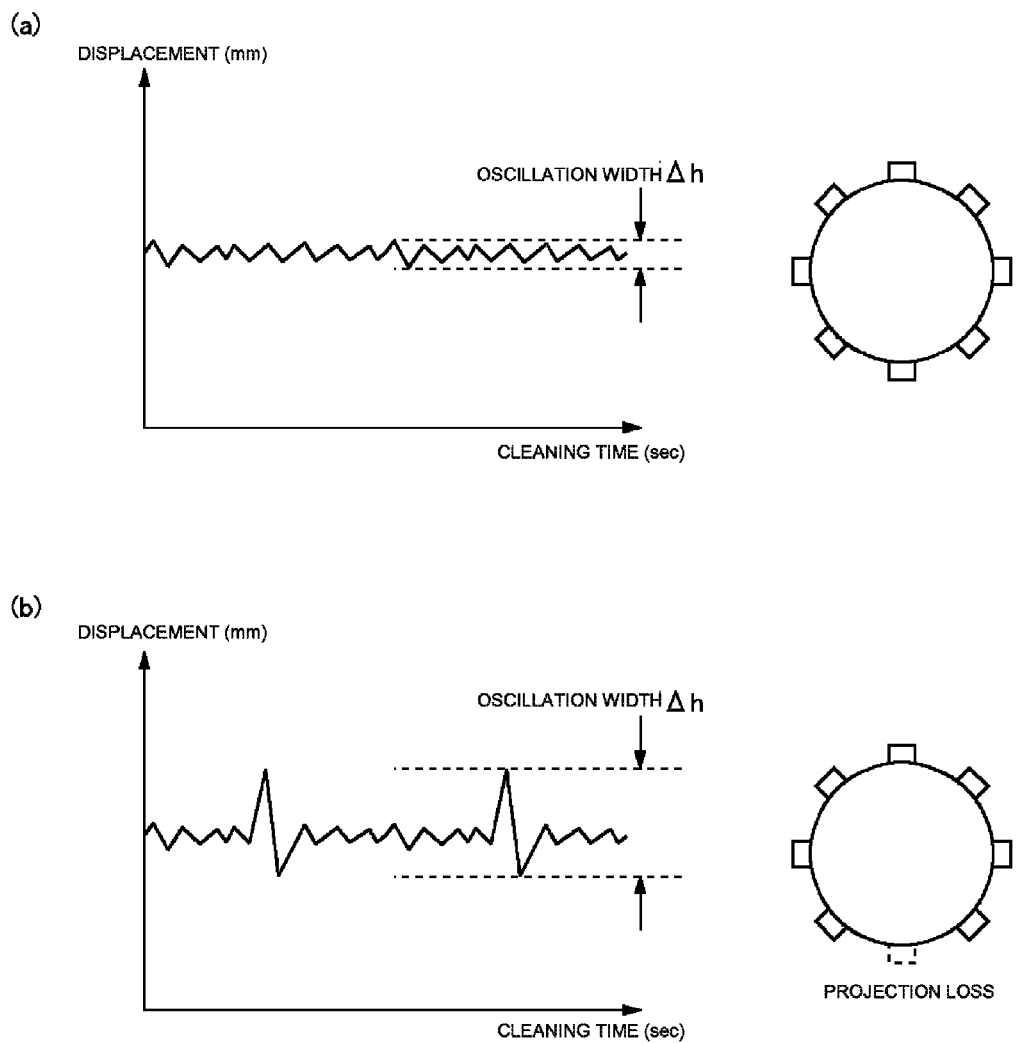
FIG. 5 is a view illustrating the change in the cleaning position of the holding means (displacement) while a single substrate is cleaned in this embodiment.

Also, the control device 11 detects presence/absence of abnormality in the cleaning member 2 from the change in the cleaning position while a single substrate W is scrubbed and cleaned. In particular, the control device 11 detects that there is abnormality in the cleaning member 2 when the amount of change in the cleaning position becomes greater than a predetermined reference amplitude. FIG. 5 is a view illustrating the change in the cleaning position (displacement) while a single substrate W is cleaned. As shown in FIG. 5(A), when there is not abnormality in the cleaning member 2, the amount of change in the cleaning position (an oscillation width $\Delta h$) falls within the range of the predetermined reference amplitude while a single substrate W is cleaned.

On the one hand, as shown in FIG. 5(B), while the cleaning member 2 is continuously used, a partial loss (a projection loss or the like) may occur in the surface of the cleaning member 2. In such a situation, oscillation arising from the loss occurs while a single substrate W is cleaned, and the amount of change in the cleaning position (the oscillation width $\Delta h$) exceeds the predetermined reference amplitude while the single substrate W is cleaned. In this way, occurrence of a projection loss or the like is detected as the change in the cleaning position.

Figure 6:
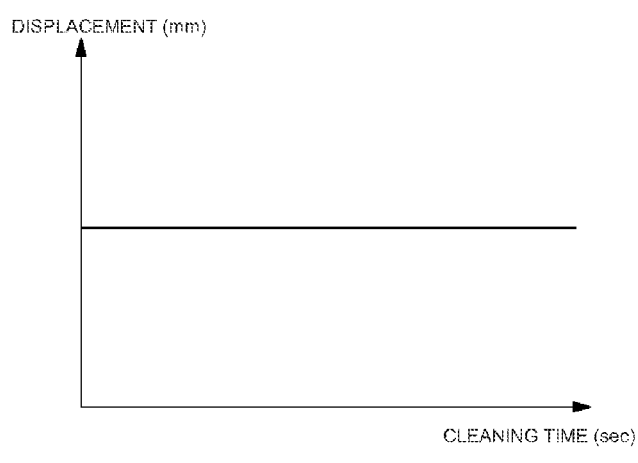
FIG. 6 is a view illustrating the change in the position of the holding means (displacement) with a vibration noise removed (canceled) in this embodiment.
Figure 6:
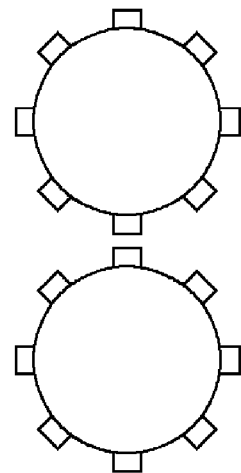
Figure 6:
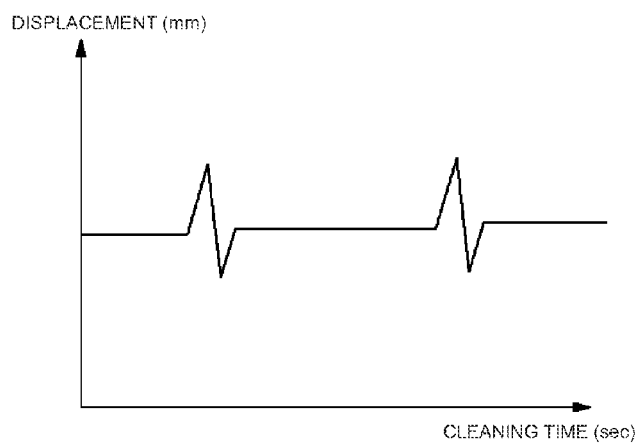
Figure 6:
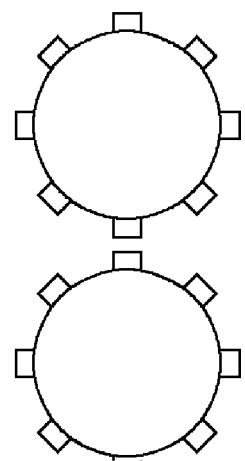

Furthermore, the control device 11 has a function that, when a substrate W is put between two cleaning members 2 to scrub and clean the substrate, removes a noise (a vibration noise) on measuring the cleaning position by a difference processing of change in the cleaning position of the two cleaning members 2. FIG. 6 is a view illustrating the change in the cleaning position (the change in the cleaning position while a single substrate W is cleaned) with a vibration noise removed (canceled). As shown in FIG. 6(A), when there is not abnormality in the cleaning members 2, the vibration noise is canceled and the amount of change in the cleaning position (oscillation width $\Delta h$) is suppressed to be very small. In this situation, as shown in FIG. 6(B), when there is abnormality (for example, a partial loss) in the cleaning member 2, oscillation arising from the loss can be detected with a high accuracy (a high S/N ratio).

According to such a substrate cleaning apparatus 1 of this embodiment, while a plurality of substrates W are continuously scrubbed and cleaned, the replacement time of the cleaning member 2 can be appropriately determined from the change in the cleaning position. In such a situation, it is not necessary to use a workpiece for checking as in the conventional, allowing an enhanced throughput and a decreased cost by that amount to be achieved.

That is, in this embodiment, while a substrate W is scrubbed and cleaned, as the pressing amount of the cleaning member 2 against the substrate W (a crushed amount of the cleaning member), the cleaning position (the position of the holding member 6 or the arm 7 when the cleaning member 2 abuts on the substrate) is measured. The cleaning member 2, while continuously used, deforms or wears, and the pressing amount (the crushed amount) becomes large. Accordingly, after a plurality of substrates W are continuously cleaned, the cleaning position (the pressing amount of the cleaning member 2) changes. Thus, the replacement time of the cleaning member 2 can be appropriately determined from change in the cleaning position while the plurality of substrates W are continuously scrubbed and cleaned.

In particular, as shown in FIG. 4(A), while a plurality of substrates W are continuously scrubbed and cleaned, when the amount of change in the cleaning position becomes greater than a predetermined reference value (threshold value), it is determined that the replacement time of the cleaning member 2 is reached. As described above, the amount of change in the cleaning position is compared with the predetermined reference value and the replacement time of the cleaning member 2 can be appropriately determined.

Also, while the cleaning member 2 is continuously used, a partial loss may occur in the surface of the cleaning member 2. In such a situation, oscillation arising from the loss occurs while a substrate W is cleaned, and the loss occurrence is detected as change in the cleaning position (the position of the holding member 6 or the arm 7 when the cleaning member 2 abuts on the substrate). Accordingly, from the change in the cleaning position while a single substrate W is cleaned, presence/absence of abnormality (for example, occurrence of a partial loss) in the cleaning member 2 can be appropriately detected.

In particular, as shown in FIG. 5(B), while a single substrate W is scrubbed and cleaned, when the amount of change in the cleaning position (oscillation width $\Delta h$) becomes greater than a predetermined reference amplitude, it is determined that there is abnormality (a projection loss) in the cleaning member 2. As described above, the amount of change in the cleaning position (oscillation width $\Delta h$) is compared with the predetermined reference amplitude and presence/absence of abnormality in the cleaning member 2 can be appropriately determined.

Also, in this embodiment, as the position measuring means of the holding member 6 and the arm 7, the displacement sensor 9 is used. The position measuring bracket 10 provided in the holding member 6 and the arm 7 is irradiated with the position measurement laser beam, reflected light (position measurement laser beam) from the position measuring bracket 10 is detected by the displacement sensor 9, and from the detection result, the position of the holding member 6 and the arm 7 is measured. In this way, the position of the holding member 6 and the arm 7 (cleaning position) can be contactlessly measured.

Furthermore, in this embodiment, when a substrate W is put between two cleaning members 2 placed above and below the substrate and the substrate is cleaned, the cleaning position of respective cleaning members 2 is measured. While a substrate is cleaned by using the cleaning member 2, a vibration noise may occur, and this vibration noise (a very small oscillation compared with the oscillation occurring when there is a partial loss in the cleaning member 2) is thought to occur to a similar degree in the two cleaning members 2 placed above and below the substrate W, so that the vibration noise can be removed (canceled) by a difference processing of the change in the cleaning position of the holding member 6 or the arm 7 of the two cleaning members 2. This can allow the change in the position of the holding member 6 or the arm 7 (cleaning position) to be measured with a high accuracy.

Furthermore, in this embodiment, a deformation amount of the cleaning member 2 can be directly monitored. In contrast, when the deformation amount of the cleaning member 2 is indirectly monitored, for example, when motor torque of a motor that rotates a substrate W is monitored, it is thought that there is an effect other than the effect of the cleaning member 2. For example, the motor torque changes depending on the state of other components involved in rotary operation of the substrate W (a seal member such as an O-ring, a timing belt that transmits rotary drive and the like). Additionally, the motor torque changes also depending on the state of the surface of the substrate W (a kind of substrate, a flow rate of a rinse and the like) because a friction resistance on the surface of the substrate W changes. As described above, the detection by using the motor torque includes a plurality of factors other than the cleaning member 2, so that it is difficult to detect the change in the motor torque as the change in the cleaning member 2 itself. According to this embodiment, the deformation amount of the cleaning member 2 is directly monitored, and accordingly it is easy to detect the change in the cleaning member 2 itself because there is not an effect of a factor other than the cleaning member 2.

Figure 7:
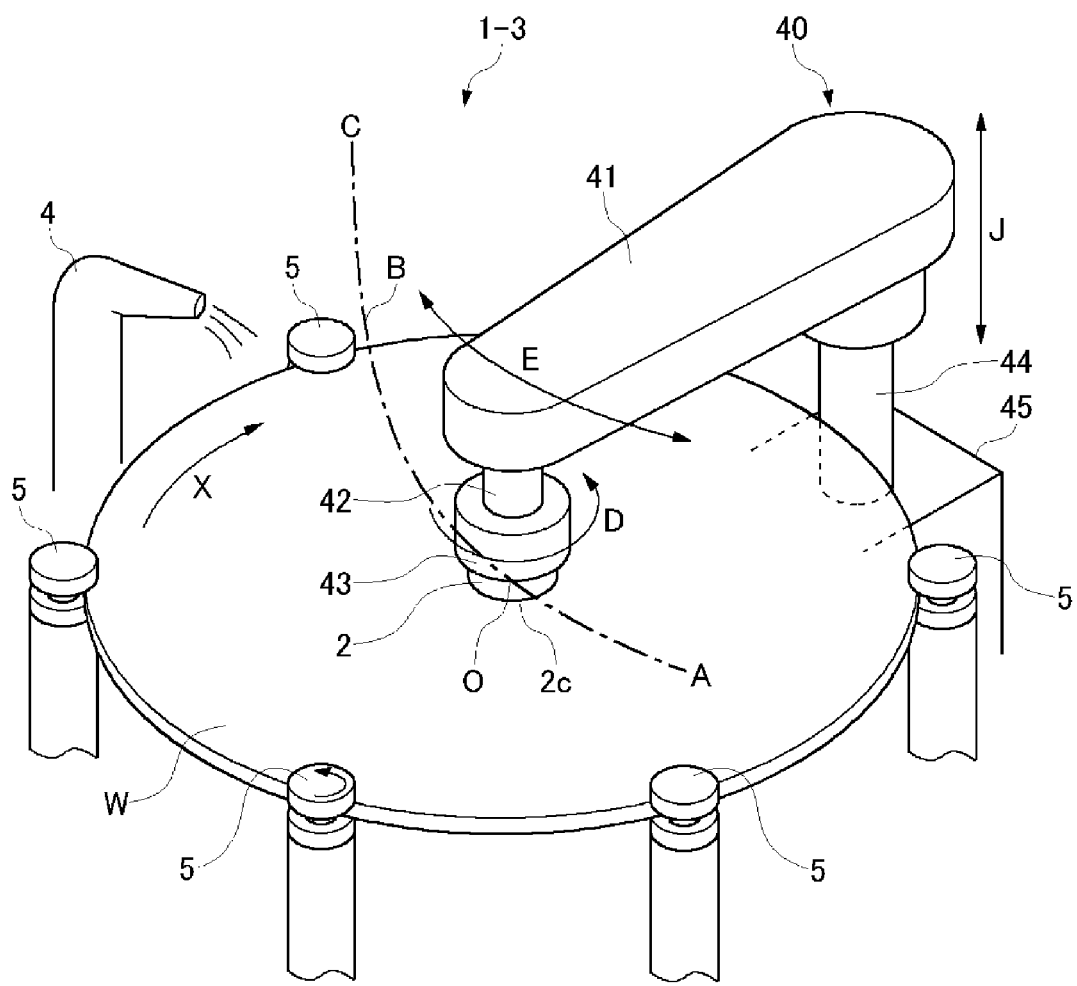
FIG. 7 is a perspective view illustrating a configuration of a substrate cleaning apparatus in another embodiment.

For example, FIG. 7 is a view illustrating a configuration example of a substrate cleaning apparatus according to another embodiment. The substrate cleaning apparatus 1-3 shown in FIG. 7 uses a pencil-type sponge as the cleaning member 2, instead of the roll sponge used as the cleaning member 2 in the substrate cleaning apparatus 1 shown in FIG. 1. This cleaning member (hereinafter, called a "pencil-type sponge") 2 is made from foamed polyurethane, PVA or the like and formed in a form such as a columnar form or a trapezoidal form, in which a cleaning surface 2c provided in the lower surface of the pencil-type sponge 2 abuts on a substrate W while rotating around a shaft (rotary shaft 42) perpendicular to the cleaning surface 2c in the horizontal plane. A configuration of other portions in the substrate cleaning apparatus 1-3 is similar to the substrate cleaning apparatus 1, the description of which will be omitted here.

The pencil-type sponge 2 is held by a cleaning member holding mechanism 40. The cleaning member holding mechanism 40 has a swinging arm 41 extending in the horizontal direction, and in the tip of the swinging arm 41, the rotary shaft 42 is provided vertically downward, and on the tip of the rotary shaft 42, the pencil-type sponge 2 held by a holding fixture 43 is mounted. The rotary shaft 42 is driven by a rotation mechanism not shown to rotate in the direction shown by the arrow D, rotating the pencil-type sponge 2 in the same direction. Also, in the rear end portion of the swinging arm 41, a swinging shaft 44 and a drive unit 45 are provided and these swing the swinging arm 41 in the direction shown by the arrow E and move it up and down in the direction shown by the arrow J.

In the substrate cleaning apparatus 1-3 having the above configuration, a cleaning liquid such as deionized water is supplied from the cleaning liquid supply nozzle 4 to the upper surface of a substrate W that is held and rotated by the spindles 5 in the direction shown by the arrow X in FIG. 7, and simultaneously the pencil-type sponge 2 is moved down while made to rotate at a predetermined, constant number of revolutions, thereby abutting the cleaning surface 2c on the upper surface of the substrate W at a position A (cleaning start position) by a predetermined press force or pressing amount. From this state, the swinging arm 41 is swung in the direction shown by the arrow E so that the pencil-type sponge 2 passes a position O that is the center position of rotation of the substrate W, thereby rubbing the upper surface of the substrate W with the pencil-type sponge 2 to scrub and clean the substrate W. After the scrubbing and cleaning, the swinging arm 41 is moved up and turned, thereby moving the pencil-type sponge 2 through a position B that is a cleaning, outer circumferential position to a position C that is a shelter position.

Note that the cleaning member 2 may be provided in both surfaces of a substrate W, or in one surface of the substrate W. Additionally, if the cleaning member 2 is provided in both surfaces of the substrate W, only the roll sponge may be used, only the pencil-type sponge may be used, or a combination of the roll sponge and the pencil-type sponge may be used.

Figure 8:
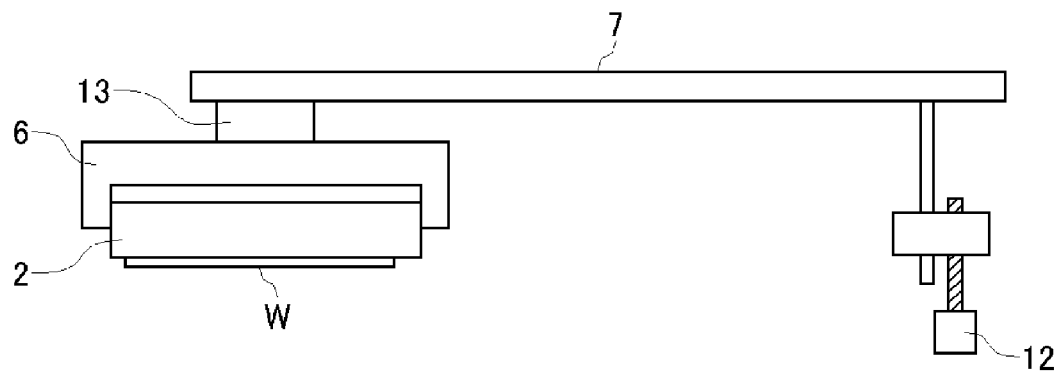
FIG. 8 is a perspective view illustrating a configuration of a substrate cleaning apparatus in yet another embodiment.

Also, FIG. 8 is a perspective view illustrating a configuration of a substrate cleaning apparatus in yet another embodiment. In the substrate cleaning apparatus 1 shown in FIG. 2, the air cylinder 8 is used as the means that generates force to press the cleaning member 2 against a substrate W and the displacement sensor 9 is used as the means that measures a position of the arm 7 (and the holding member 6), but a servo motor 12 may be used as shown in FIG. 8.

In such a situation, in an attaching portion of the arm 7, a load cell 13 is provided to measure a pressing force (load), and the servo motor 12 is made to rotate until a constant load is applied to the load cell 13. A number of revolutions and a phase of the servo motor 12 can be sensed by the servo motor 12 itself, accordingly a position of the arm 7 (cleaning position) is recorded when the constant load is reached, change in the cleaning position for each substrate W is measured, and from the change in the cleaning position, the replacement time of the cleaning member 2 can be determined.

Figure 9:
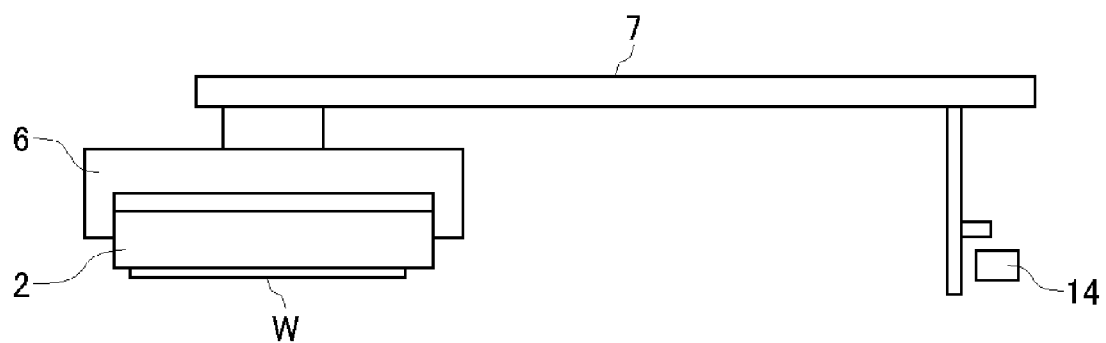
FIG. 9 is a perspective view illustrating a configuration of a substrate cleaning apparatus in further yet another embodiment.

Furthermore, FIG. 9 is a perspective view illustrating a configuration of a substrate cleaning apparatus in further yet another embodiment. In the substrate cleaning apparatus 1 shown in FIG. 2, the air cylinder 8 is used as the means that generates force to press the cleaning member 2 against a substrate W and the displacement sensor 9 is used as the means that measures a position of the arm 7 (and the holding member 6), but a contact sensor 14 may be used as shown in FIG. 9.

For example, the crushed amount corresponding to the replacement time of the cleaning member 2 (the crushed amount corresponding to the replacement time) is preliminarily measured and grasped, and the contact sensor 14 detects that the arm 7 (and the holding member 6) reaches that position (the crushed position by the crushed amount corresponding to the replacement time), thereby allowing the replacement time of the cleaning member 2 to be determined.

Figure 10:
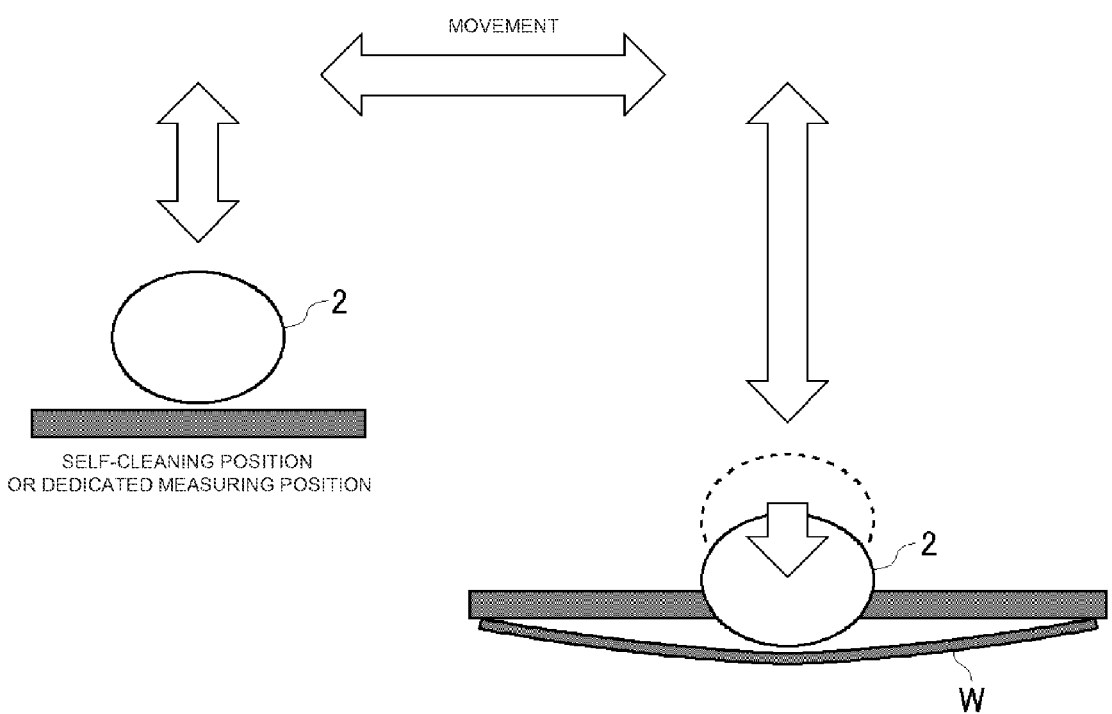
FIG. 10 is an illustration showing a measuring position at which an amount of change is measured in further yet another embodiment.

Additionally, in the above example, the example where the amount of change in the cleaning position is measured has been described, but the position at which the amount of change is measured is not limited to the cleaning position. For example, as shown in FIG. 10, the position at which the amount of change is measured may be a self-cleaning position of the cleaning member. Also, a dedicated position at which the amount of change is measured (dedicated measuring position) may be provided in a module. At the self-cleaning position and the dedicated measuring position, only the amount of change in the cleaning member 2 can be measured without an effect of force to press the cleaning member 2 against a substrate W and an effect of a deformation of the substrate W due to its own weight. The measurement of the amount of change at the self-cleaning position and the dedicated measuring position is particularly suitable when a thickness and/or the amount of change is different depending on a substrate W to be processed.

Figure 11:
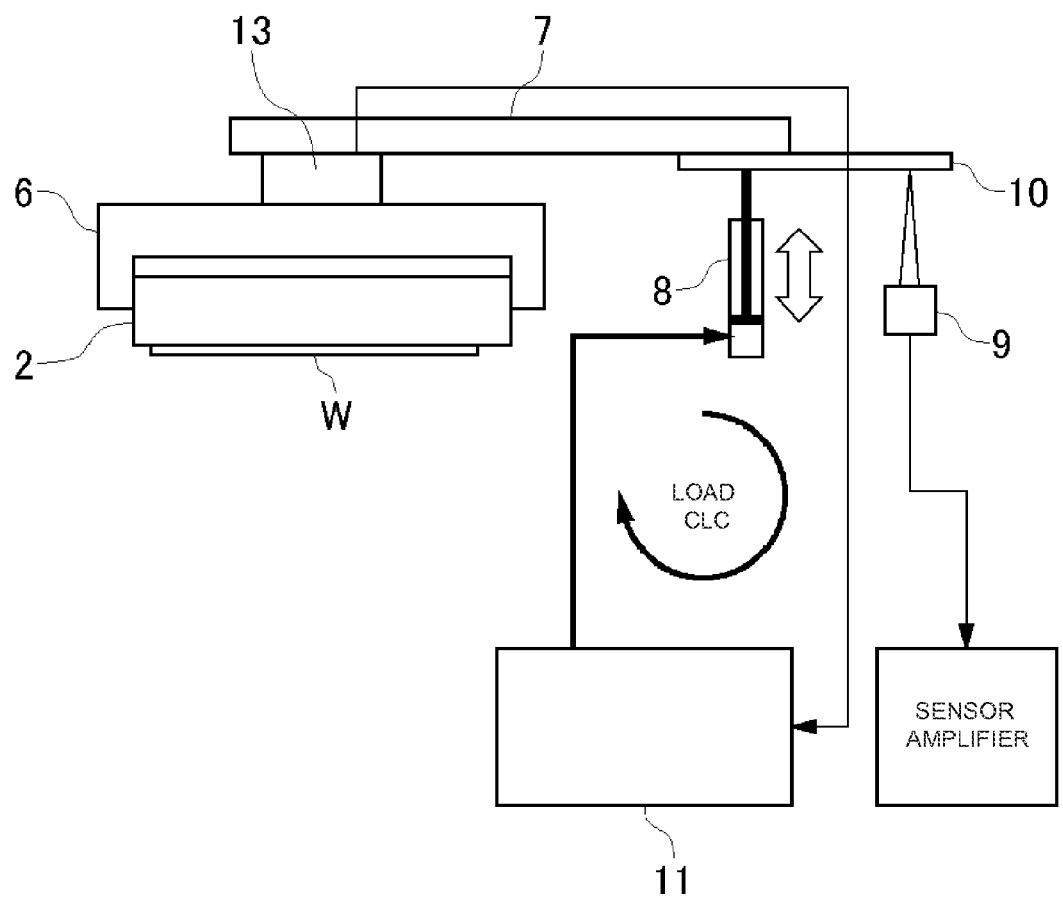
FIG. 11 is a perspective view illustrating a configuration of a substrate cleaning apparatus in further yet another embodiment.

Also, as shown in FIG. 11, the control device 11 may have a load CLC (Closed Loop Control) function. When the amount of change in the cleaning position reaches the predetermined reference value, the control device 11, by using the load CLC, controls the air cylinder 8 so that the cleaning position takes a position immediately after replacement. Then, this process is repeated, and after a predetermined number of times elapsed, it is determined that the replacement time of the cleaning member is reached.

In a situation of the load CLC, the load cell 13 is provided in the arm 7 and a press load is concurrently measured, accordingly the pressing force can be controlled by feeding back an actual press load and the actual press load can be compared with the deformation amount of the sponge of the cleaning member 2, allowing management to be performed with a higher accuracy. If a sliding friction changes due to wear or the like of components in a lifting mechanism such as the air cylinder 8, an actually applying load deviates without the operation of the CLC, so that it is difficult to distinguish between the change in the cleaning member 2 and the change in other components. For example, let the pressing force of the cleaning member 2 be 4 N and the displacement be 1 mm in the initial time of use. Supposing that the air cylinder 8 wears and the sliding resistance increases by 1 N during use, force to actually press the cleaning member 2 decreases due to the friction and becomes equivalent to 3 N. Therefore, even if the cleaning member 2 is normal, the deformation amount of the cleaning member 2 has only the crushed amount by the pressing force of 3 N and an actual change in the cleaning member 2 cannot be accurately monitored. In contrast, if the load CLC function is provided, the pressing load can be kept constant, allowing the deformation amount of only the cleaning member 2 to be monitored.

Figure 12:
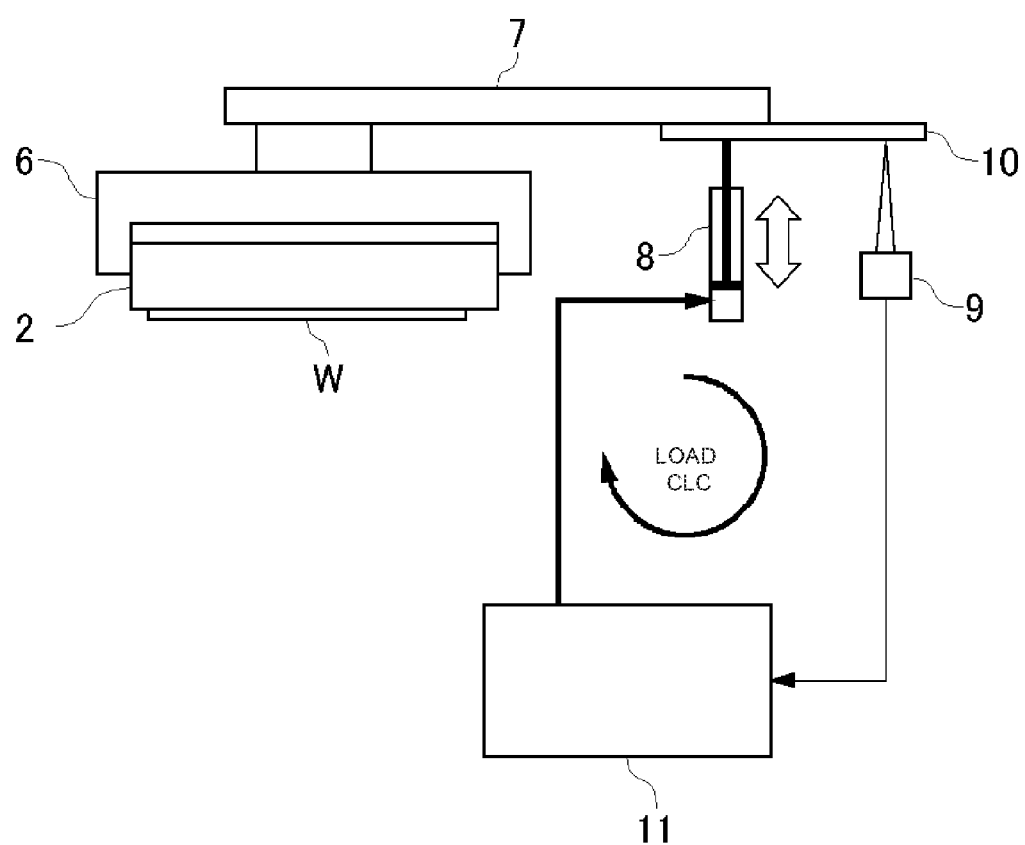
FIG. 12 is a perspective view illustrating a configuration of a substrate cleaning apparatus in further yet another embodiment.

Furthermore, as shown in FIG. 12, the control device 11 may have a position CLC (Closed Loop Control) function. In such a situation, the control device 11 performs the position CLC by using the measured value of the displacement sensor. Because of operation of the position CLC, the cleaning member 2 can be reliably pressed by a constant amount, allowing a contact area of the cleaning member 2 to be kept constant.

What is claimed is:

1. A replacement time determining method of a cleaning member in a substrate cleaning apparatus that scrubs and cleans a substrate, comprising:
   measuring a first position of a holding member that holds the cleaning member when the cleaning member abuts on the substrate; and
   measuring a second position of the holding member when the cleaning member stays away from the substrate;
   determining a replacement time of the cleaning member based on a change in the first position while a plurality of substrates are scrubbed and cleaned.

2. The replacement time determining method according to claim 1, comprising:
   measuring force to press the cleaning member against the substrate; and
   controlling the force to press the cleaning member against the substrate by feeding back a measured result of measuring the force.

3. An abnormality detecting method in a cleaning member of a substrate cleaning apparatus that scrubs and cleans a substrate, comprising:
   measuring a first position of a holding member that holds the cleaning member when the cleaning member abuts on the substrate; and
   a second position of the holding member when the cleaning member stays away from the substrate;
   detecting presence/absence of abnormality in the cleaning member based on the position change in the first position while a single substrate is scrubbed and cleaned.

4. A substrate cleaning apparatus, comprising:
   a cleaning member that abuts on a substrate to scrub and clean the substrate;
   a holding member that holds the cleaning member, the holding member being connected to an arm;
   an air cylinder or a servo motor that generates force to press the cleaning member against the substrate, the air cylinder or the servo motor being connected to the arm;
   a position measuring sensor that is provided in the holding member and/or the arm, and measures
     a first position of the holding member when the cleaning member abuts on the substrate, and
     a second position of the holding member when the cleaning member stays away from the substrate; and
   a controller that determines a replacement time of the cleaning member based on change in the first position of the holding member while a plurality of substrates are continuously scrubbed and cleaned.

5. The substrate cleaning apparatus according to claim 4, wherein
   when an amount of change in the first position becomes greater than a predetermined reference value, the controller determines that the replacement time of the cleaning member is reached.

6. The substrate cleaning apparatus according to claim 4, wherein
   the position measuring sensor is a displacement sensor that utilizes a position measurement laser beam, and
   the holding member is provided with a position measuring bracket which is irradiated with the position measurement laser beam.

7. The substrate cleaning apparatus according to claim 4, comprising:
   a load cell that measures force to press the cleaning member against the substrate; and
   a load controller that controls the force to press the cleaning member against the substrate by feeding back the measured result of the load cell.

8. The substrate cleaning apparatus according to claim 4, wherein
   two cleaning members are placed above and below the substrate so that the substrate is put between them and the first positions of the two cleaning members each are measured by a corresponding position measuring sensor, comprising:
   a noise remover that removes a noise on measuring the first position by a difference processing of change in the first positions of the two cleaning members when the substrate is put between the two cleaning members to scrub and clean the substrate.

9. A substrate cleaning apparatus, comprising:
   a cleaning member that abuts on a substrate to scrub and clean the substrate;
   a holding member that holds the cleaning member, the holding member being connected to an arm;
   an air cylinder or a servo motor that generates force to press the cleaning member against the substrate, the air cylinder or the servo motor being connected to the arm;
   a position measuring sensor that is provided in the holding member and/or the arm, and measures
     a first position of the holding member when the cleaning member abuts on the substrate, and
     a second position of the holding member when the cleaning member stays away from the substrate; and
   a controller that determines the presence and/or absence of abnormality in the cleaning member based on change in the first position of the holding member while a single substrate is scrubbed and cleaned.

10. The substrate cleaning apparatus according to claim 9, wherein the controller detects that there is abnormality in the cleaning member when an amount of change in the first position becomes greater than a predetermined reference amplitude.

11. The substrate cleaning apparatus according to claim 9, wherein the position measuring sensor is a displacement sensor that utilizes a position measurement laser beam, and the holding member is provided with a position measuring bracket which is irradiated with the position measurement laser beam.

12. The substrate cleaning apparatus according to claim 9, comprising:

a load cell that measures force to press the cleaning member against the substrate; and a load controller that controls the force to press the cleaning member against the substrate by feeding back the measured result of the load cell.

13. The substrate cleaning apparatus according to claim 9, wherein two cleaning members are placed above and below the substrate so that the substrate is put between them and the first positions of the two cleaning members each are measured by a corresponding position measuring sensor, comprising:

a noise remover that removes a noise on measuring the first position by a difference processing of change in the first positions of the two cleaning members when the substrate is put between the two cleaning members to scrub and clean the substrate.

* * * * *